US008920738B2

(12) United States Patent
Elgat et al.

(10) Patent No.: US 8,920,738 B2
(45) Date of Patent: Dec. 30, 2014

(54) METHOD FOR SAFELY PROCESSING A FLUID VIA MONITORING AND DECREASING EXPLOSIVENESS

(71) Applicant: Elcon Recycling Center (2003) Ltd., Haifa (IL)

(72) Inventors: Zvi Elgat, Reut (IL); Yaron Aviezer, Moshav Nahalal (IL)

(73) Assignee: Elcon Recycling Center (2003) Ltd., Haifa (IL)

( * ) Notice: Subject to any disclaimer, the term of this patent is extended or adjusted under 35 U.S.C. 154(b) by 0 days.

(21) Appl. No.: 14/102,521

(22) Filed: Dec. 11, 2013

(65) Prior Publication Data
US 2014/0097077 A1 Apr. 10, 2014

Related U.S. Application Data

(62) Division of application No. 12/810,861, filed as application No. PCT/IB2008/055567 on Dec. 29, 2008, now Pat. No. 8,647,582.

(60) Provisional application No. 61/009,214, filed on Dec. 27, 2007.

(51) Int. Cl.
*B01D 50/00* (2006.01)
*G01N 25/54* (2006.01)
*B01J 19/00* (2006.01)

(52) U.S. Cl.
CPC .............. *G01N 25/54* (2013.01); *B01J 19/002* (2013.01); *B01J 2219/00108* (2013.01); *B01J 2219/00186* (2013.01); *B01J 2219/00198* (2013.01); *B01J 2219/00202* (2013.01); *B01J 2219/00238* (2013.01); *B01J 2219/00263* (2013.01); *Y10S 588/90* (2013.01)
USPC .......................................... 422/169; 588/900

(58) Field of Classification Search
USPC ........... 422/168, 169; 588/403, 900; 502/401, 502/439
See application file for complete search history.

(56) References Cited

U.S. PATENT DOCUMENTS

| | | | |
|---|---|---|---|
| 3,770,059 A | 11/1973 | Graham | |
| 3,945,890 A | 3/1976 | Kemp | |
| 4,098,303 A | 7/1978 | Gammell | |
| 4,188,793 A | 2/1980 | Watson et al. | |
| 4,260,573 A | 4/1981 | Overman | |
| 4,276,835 A | 7/1981 | Zeltner | |
| 4,304,198 A | 12/1981 | Stiefel | |
| 4,482,696 A | 11/1984 | Schuster et al. | |
| 4,693,786 A | 9/1987 | Brett et al. | |
| 4,804,632 A | 2/1989 | Schuck et al. | |
| 4,857,458 A | 8/1989 | Nobilet et al. | |
| 4,871,426 A | 10/1989 | Lechert et al. | |
| 4,929,312 A | 5/1990 | Westcott | |
| 5,053,200 A | 10/1991 | Schaeffer et al. | |
| 5,106,571 A | 4/1992 | Wade et al. | |
| 5,454,177 A | 10/1995 | Dutournier | |
| 5,596,129 A | 1/1997 | Murashige et al. | |
| 6,346,420 B1 | 2/2002 | Miric et al. | |
| 8,647,582 B2 * | 2/2014 | Elgat et al. ..................... | 422/169 |
| 2002/0108865 A1 | 8/2002 | Bryan et al. | |
| 2004/0097774 A1 | 5/2004 | Hall et al. | |
| 2004/0099045 A1 | 5/2004 | Demarest et al. | |
| 2006/0003402 A1 | 1/2006 | Adris et al. | |
| 2006/0196358 A1 | 9/2006 | Levin | |
| 2006/0216663 A1 | 9/2006 | Morrissey | |
| 2012/0090979 A1 | 4/2012 | Elgat et al. | |

FOREIGN PATENT DOCUMENTS

| | | |
|---|---|---|
| CA | 1073052 | 3/1980 |
| CA | 1103146 | 6/1981 |
| CA | 2032947 | 2/2004 |
| CN | 1781594 | 6/2006 |
| DE | 19959834 | 8/2001 |
| EP | 0624396 | 11/1994 |
| EP | 09-313803 | 12/1997 |
| EP | 1031829 | 8/2000 |
| EP | 1055927 | 10/2004 |
| EP | 1658893 | 5/2006 |
| GB | 190917210 | 7/1910 |
| GB | 1525020 | 8/1978 |
| JP | 57-004535 | 1/1982 |

(Continued)

OTHER PUBLICATIONS

Office Action Dated Mar. 13, 2014 From the State Intellectual Property Office of the People's Republic of China Re. Application No. 200880127593.0 and Its Translation Into English.

(Continued)

*Primary Examiner* — Edward Johnson

(57) ABSTRACT

Safely processing fluid via monitoring and decreasing explosiveness of vapor-gas species formed therefrom, or contained therein. Fluid input unit 12, for transporting source fluid 24; first fluid processing unit 14, for receiving and processing fluid 26, and forming processed fluid including vapor-gas portion 30; vapor-gas explosiveness monitoring and decreasing unit 16, for measuring at least an indication of explosiveness level of vapor-gas portion 30, wherein if the measurement exceeds a pre-determined threshold explosiveness level (PDTEL), then vapor-gas portion 30 is condensed, for forming condensate and output vapor-gas 32 whose explosiveness level is less than lower explosion limit (LEL) of output vapor-gas 32; second fluid processing unit 18, for processing output vapor-gas 32, and forming processed vapor-gas product 34. Includes an output unit 20 for transporting processed vapor-gas product 34 as (vapor-gas, liquid, or/and solid) output products 36, for disposal, storage, or/and additional processing, and a central process control unit 22.

32 Claims, 6 Drawing Sheets

(56) References Cited

FOREIGN PATENT DOCUMENTS

| JP | 11-244602 | 9/1999 |
| JP | 2000-292590 | 10/2000 |
| JP | 2008-049225 | 3/2008 |
| WO | WO 00/27495 | 5/2000 |
| WO | WO 03/062517 | 7/2003 |
| WO | WO 2009/083931 | 7/2009 |

OTHER PUBLICATIONS

International Preliminary Report on Patentability Dated Jul. 8, 2010 From the International Bureau of WIPO Re. Application No. PCT/IB2008/055567.

International Search Report Dated Jul. 6, 2009 From the International Searching Authority Re.: Application No. PCT/M2008/055567.

Notice of Allowance Dated Sep. 23, 2013 From the US Patent and Trademark Office Re. U.S. Appl. No. 12/810,861.

Office Action Dated Sep. 30, 2013 From the State Intellectual Property Office of the People's Republic of China Re. Application No. 200880127593.0 and Its Translation Into English.

Official Action Dated Jun. 19, 2013 From the US Patent and Trademark Office Re. U.S. Appl. No. 12/810,861.

Restriction Official Action Dated Mar. 1, 2013 From the US Patent and Trademark Office Re. U.S. Appl. No. 12/810,861.

Translation of Office Action Dated Nov. 28, 2012 From the State Intellectual Property Office of the People's Republic of China Re. Application No. 200880127593.0.

Translation of Search Report Dated Sep. 30, 2013 From the State Intellectual Property Office of the People's Republic of China Re. Application No. 200880127593.0.

Written Opinion Dated Jul. 6, 2009 From the International Searching Authority Re.: Application No. PCT/IB2008/055567.

\* cited by examiner

2

(a) Receiving and transporting the fluid; by a fluid input unit.

4

(b) Processing the fluid, for forming a processed fluid including a vapor-gas portion; by a first fluid processing unit.

6

(c) Measuring explosiveness level of the vapor-gas portion, wherein if the explosiveness level of the vapor-gas portion exceeds a pre-determined threshold explosiveness level (PDTEL), then part of the vapor-gas portion is condensed, for forming a condensate, and an output vapor-gas whose explosiveness level is less than lower explosion limit (LEL) of the output vapor-gas; by a vapor-gas explosiveness monitoring and decreasing unit.

8

(d) Processing the output vapor-gas, for forming processed vapor-gas product; by a second fluid processing unit.

FIG.1

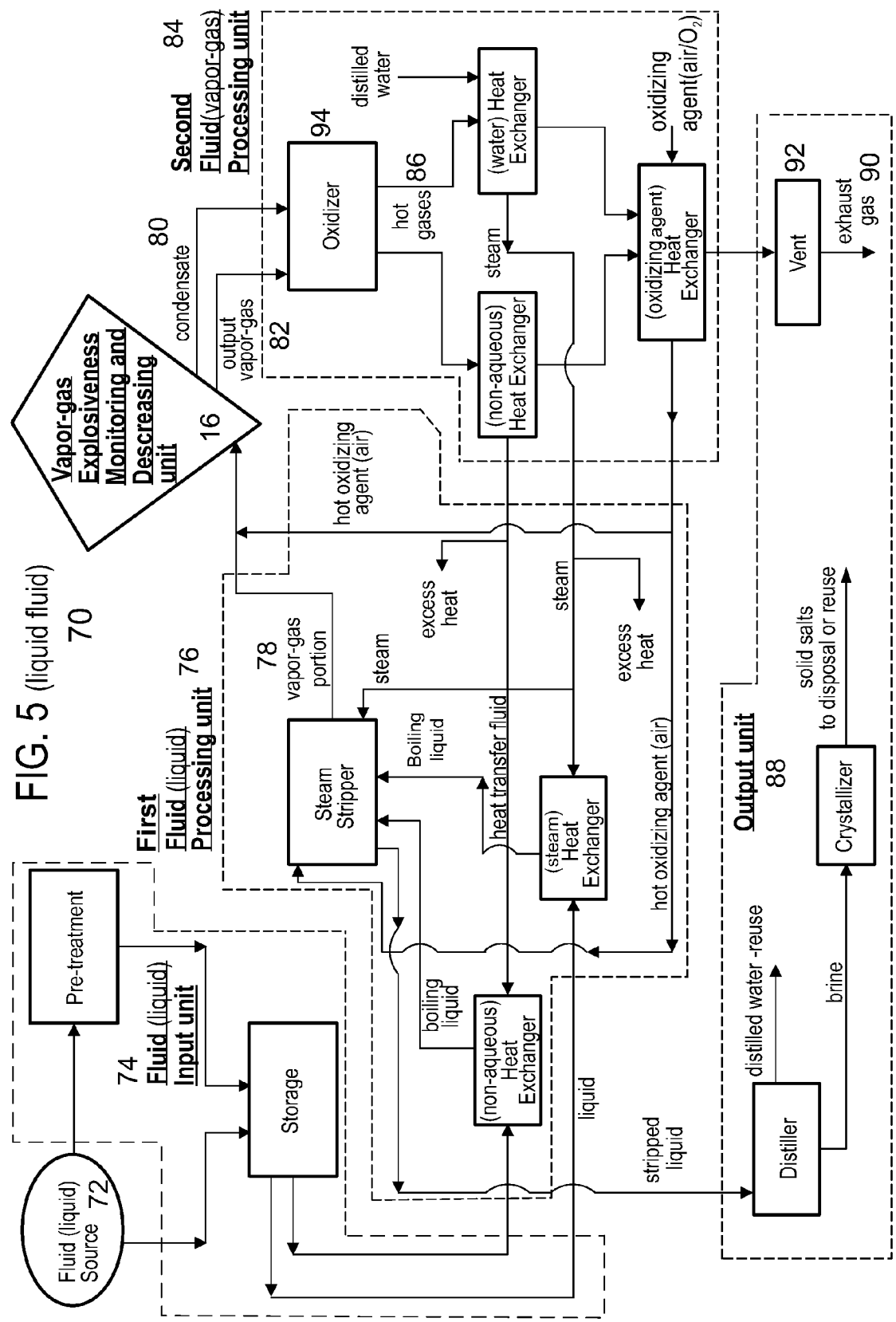

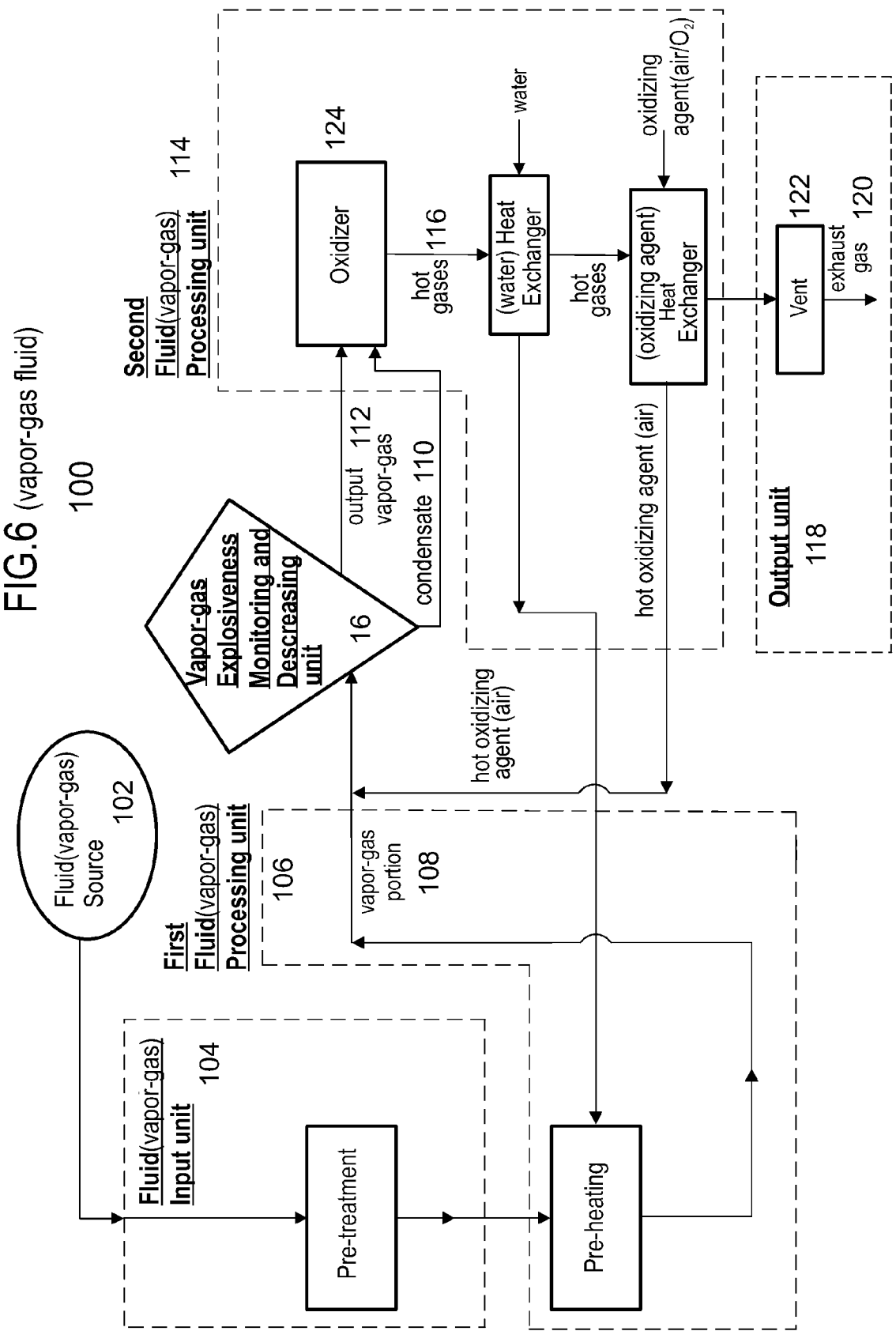

METHOD FOR SAFELY PROCESSING A FLUID VIA MONITORING AND DECREASING EXPLOSIVENESS

RELATED APPLICATIONS

This application is a division of U.S. patent application Ser. No. 12/810,861 filed on Oct. 28, 2010, which is a National Phase of PCT Patent Application No. PCT/IB2008/055567 filed on Dec. 29, 2008, which claims the benefit of priority of U.S. Provisional Patent Application No. 61/009,214 filed on Dec. 27, 2007. The contents of the above applications are all incorporated by reference as if fully set forth herein in their entirety.

FIELD OF THE INVENTION

The present invention, in some embodiments thereof, relates to safely processing a (liquid or vapor-gas) fluid, where the processing involves vapor-gas species that are explosive, and more particularly, but not exclusively, to safely processing a fluid via monitoring and decreasing explosiveness of vapor-gas species formed therefrom, or contained therein. Some embodiments of the present invention are generally relevant to a wide variety of different fields of technology which involve essentially any type or kind, and scale (size), of processing of essentially any type or kind of liquid fluid or vapor-gas fluid, where processing of the fluid involves explosive (combustible) vapor-gas species. Some embodiments of the present invention are generally relevant to those fields of technology which require safe processing of a liquid or vapor-gas fluid that involves explosive (combustible) vapor-gas species being volatile (combustible) compounds, such as volatile (combustible) organic or/and inorganic compounds. Some embodiments of the present invention are particularly relevant to the field of technology which involves safe processing of a fluid, where the fluid is a liquid being contaminated water, such as industrial wastewater, contaminated with volatile (combustible) organic or/and inorganic compounds, and the processing is based on safely removing the water contaminants from (i.e., decontaminating or purifying) the contaminated water (wastewater). Some embodiments of the present invention are also particularly relevant to the field of technology which involves safe processing of a fluid, where the fluid is a vapor-gas being contaminated air, such as industrial waste exhaust, contaminated with volatile (combustible) organic or/and inorganic compounds, and the processing is based on safely removing the air contaminants from (i.e., decontaminating or purifying) the contaminated air (waste exhaust).

BACKGROUND OF THE INVENTION

Processing of fluids, in general, and, processing of liquid or/and vapor-gas fluids, in particular; processing (decontaminating, purifying, treating, reacting, synthesizing) [contaminated (waste), non-contaminated (clean, pure)] [aqueous, non-aqueous] (liquid) fluids or (vapor-gas) fluids; processing and handling of explosive (combustible) vapor-gas species, such as volatile (combustible) organic or/and inorganic compounds; and, physicochemical properties, characteristics, and behavior of explosive (combustible) vapor-gas species; theories, principles, and practices thereof, and, related and associated applications and subjects thereof, are well known and taught about in scientific, technical, and patent, literature, and currently practiced in a wide variety of numerous different fields and areas of technology.

Essentially any type or kind, and scale (size), of processing of essentially any type or kind of liquid fluid or vapor-gas fluid, where processing of the fluid involves explosive (combustible) vapor-gas species, particularly where explosive (combustible) vapor-gas species (for example, as intermediate or final products) are formed while processing the fluid, or are contained in the (initial or starting) fluid, is potentially dangerous due to the presence of the explosive (combustible) vapor-gas species. This applies to processing (decontaminating, purifying, treating, reacting) contaminated (waste) fluids that are in the form of aqueous or non-aqueous (liquid) fluids or (vapor-gas) fluids, as well as to processing (treating, reacting, synthesizing) non-contaminated (clean, pure) fluids that are in the form of aqueous or non-aqueous (liquid) fluids or (vapor-gas) fluids. Moreover, the preceding is applicable regardless of the scale (size) of the fluid processing, be it of a small size scale, such as that typically associated with a research laboratory; or of a medium size scale, such as that typically associated with a process/product development laboratory or facility, or associated with a pilot plant facility; or of a large (commercial or industrial) size scale, such as that typically associated with a commercial or industrial type of manufacturing, production, or processing facility. In each of these cases, where explosive (combustible) vapor-gas species are formed while processing the fluid, or are contained in the (initial or starting) fluid, there is potential (explosive) danger (to human life, as well as to physical infrastructure) due to the presence of the explosive (combustible) vapor-gas species.

For example, the applicant of the present invention has performed extensive work and developed inventions [e.g., as disclosed in references 1, 2] in the field(s) encompassing processing (decontaminating, purifying, treating, reacting (via thermal oxidation)) industrial contaminated water (industrial wastewater), contaminated with volatile (combustible) organic or/and inorganic compounds, where explosive (combustible) vapor-gas species are formed (as intermediate or final products), while processing the wastewater. As taught therein, in some embodiments, part of the overall wastewater treatment process involves the formation of explosive (combustible) vapor-gas species (particularly, those originating from volatile (combustible) organic or/and inorganic compounds contained in the wastewater). Such explosive (combustible) vapor-gas species exit as effluent from a steam stripper and are then fed as influent into a thermal oxidizer (for example, a regenerative thermal oxidizer (RTO)) for their destruction (via thermal oxidation). The effluent vapor-gas mixture exiting the steam stripper, and continuing downstream as influent for entering the thermal oxidizer (RTO), includes a particular composition or make-up (i.e., chemical types and concentrations (distribution) thereof) of explosive (combustible) vapor-gas species, which at a given set of operating conditions, can be analyzed for determining the 'explosiveness level' (in terms of empirically measured or/and theoretically calculated explosive or flammability limits) of the vapor-gas mixture, which, in turn, is usable for determining whether the vapor-gas mixture can be considered as being 'safe' or 'unsafe' for continued processing, i.e., via entering the thermal oxidizer (RTO).

In a first exemplary scenario, the applicant observed that, under certain processing conditions, the effluent vapor-gas mixture exiting the steam stripper, and intended for entering the thermal oxidizer (RTO), included a composition or make-up of explosive (combustible) vapor-gas species that was analyzed for determining a 'safe' explosiveness level of the vapor-gas mixture, which, in turn, was used for determining that the vapor-gas mixture was considered as being 'safe' for continued processing, via entering the thermal oxidizer (RTO). In this scenario, the thermal oxidizer (RTO) was allowed to continue operating for thermally oxidizing (destroying) the volatile (combustible) organic or/and inorganic compounds, and subsequently, the remainder of the overall wastewater treatment process was able to continue operating for processing (decontaminating, purifying) the wastewater.

In a second exemplary scenario, the applicant observed that, under certain processing conditions, the effluent vapor-gas mixture exiting the steam stripper, and intended for entering the thermal oxidizer (RTO), included a composition or make-up of explosive (combustible) vapor-gas species that was analyzed for determining an 'unsafe' explosiveness level of the vapor-gas mixture, which, in turn, was used for determining that the vapor-gas mixture was considered as being 'unsafe' for continued processing, via entering the thermal oxidizer (RTO). In this scenario, in strong contrast to the preceding scenario, the thermal oxidizer (RTO) was not allowed to continue operating for thermally oxidizing (destroying) the volatile (combustible) organic or/and inorganic compounds, whereby, the thermal oxidizer (RTO) was promptly shut down, thereby preventing 'unsafe' operation of the thermal oxidizer (RTO), and subsequently, the remainder of the overall wastewater treatment process was not able to continue operating for processing (decontaminating, purifying) the wastewater.

According to the preceding first exemplary scenario, so long as the effluent explosive (combustible) vapor-gas mixture exiting the steam stripper, and intended for entering the thermal oxidizer (RTO), was determined as being 'safe', the thermal oxidizer (RTO) was allowed to continue operating for thermally oxidizing (destroying) the volatile (combustible) organic or/and inorganic compounds, and subsequently, the remainder of the overall wastewater treatment process was able to continue operating for processing (decontaminating, purifying) the wastewater. However, according to the preceding second exemplary scenario, when the effluent explosive (combustible) vapor-gas mixture exiting the steam stripper, and intended for entering the thermal oxidizer (RTO), was determined as being 'unsafe', the thermal oxidizer (RTO) was shut down and not allowed to continue operating for thermally oxidizing (destroying) the volatile (combustible) organic or/and inorganic compounds, and subsequently, the remainder of the overall wastewater treatment process was not able to continue operating for processing (decontaminating, purifying) the wastewater.

The second exemplary scenario resulted in two main problems: first, a substantial amount of process 'down time', and second, having to properly deal with, and separately process, in a 'safe' and environmentally friendly manner, the 'unsafe' explosive (combustible) vapor-gas mixture exiting the steam stripper, that was supposed to enter the thermal oxidizer (RTO) for being thermally oxidized (destroyed). Both of these main problems translated to requiring significant expenditure of undesirable costs associated with time and (human, equipment) resources, especially with respect to processing (decontaminating, purifying) the wastewater on a large (commercial or industrial) size scale.

The preceding described second exemplary scenario illustrates just one example of significant problems and limitations associated with attempting to safely process a (liquid or vapor-gas) fluid, where the processing involves vapor-gas species that are explosive. Similar types of 'problematic' scenarios are generally relevant to essentially any type or kind, and scale (size), of processing of essentially any type or kind of liquid fluid or vapor-gas fluid, where processing of the fluid involves explosive (combustible) vapor-gas species. Moreover, such types of 'problematic' scenarios are certainly not limited to the field(s) encompassing processing (decontaminating, purifying, treating, reacting (via thermal oxidation)) industrial contaminated water (industrial wastewater), contaminated with volatile (combustible) organic or/and inorganic compounds, where explosive (combustible) vapor-gas species are formed (as intermediate or final products), while processing the wastewater. Such types of 'problematic' scenarios are generally relevant to a wide variety of different fields of technology which involve fluid processing, and the need for 'safely' processing of fluids, where processing of the fluid involves explosive (combustible) vapor-gas species.

SUMMARY OF THE INVENTION

Some embodiments of the present invention address and overcome the above described 'problematic' scenarios relating to processing of fluids.

The present invention, in some embodiments thereof, relates to safely processing a (liquid or vapor-gas) fluid, where the processing involves vapor-gas species that are explosive, and more particularly, but not exclusively, to safely processing a fluid via monitoring and decreasing explosiveness of vapor-gas species formed therefrom, or contained therein. Some embodiments of the present invention are generally applicable to essentially any type or kind, and scale (size), of processing of essentially any type or kind of liquid fluid or vapor-gas fluid, where processing of the fluid involves explosive (combustible) vapor-gas species. Some embodiments of the present invention are generally applicable to safely processing a liquid or vapor-gas fluid which involves explosive (combustible) vapor-gas species being volatile (combustible) compounds, such as volatile (combustible) organic or/and inorganic compounds. In exemplary embodiments of the present invention, the fluid is a liquid being contaminated water, such as industrial wastewater, contaminated with volatile (combustible) organic or/and inorganic compounds, and the processing is based on safely removing the water contaminants from (i.e., decontaminating or purifying) the contaminated water (wastewater). In other exemplary embodiments of the present invention, the fluid is a vapor-gas being contaminated air, such as industrial waste exhaust, contaminated with volatile (combustible) organic or/and inorganic compounds, and the processing is based on safely removing the air contaminants from (i.e., decontaminating or purifying) the contaminated air (waste exhaust).

Thus, according to a main aspect of some embodiments of the present invention, there is provided a method for safely processing a fluid, the method comprising: receiving and transporting the fluid; processing the fluid, for forming a processed fluid including a vapor-gas portion; measuring at least an indication of explosiveness level of the vapor-gas portion, wherein if the measurement of the vapor-gas portion exceeds a pre-determined threshold explosiveness level (PD-TEL), then part of the vapor-gas portion is condensed, for forming a condensate, and an output vapor-gas whose explosiveness level is less than lower explosion limit (LEL) of the output vapor-gas; and processing the output vapor-gas, for forming processed vapor-gas product; and processing the output vapor-gas, for forming processed vapor-gas product.

More specifically, in relation to main components of a corresponding system, according to a main aspect of some embodiments of the present invention, there is provided a method for safely processing a fluid, the method comprising: receiving and transporting the fluid, by a fluid input unit; processing the fluid, for forming a processed fluid including a vapor-gas portion, by a first fluid processing unit (operatively connected to the fluid input unit); measuring at least an indication of explosiveness level of the vapor-gas portion, wherein if the measurement of the vapor-gas portion exceeds a pre-determined threshold explosiveness level (PDTEL), then part of the vapor-gas portion is condensed, for forming a condensate, and an output vapor-gas whose explosiveness level is less than lower explosion limit (LEL) of the output vapor-gas, by a vapor-gas explosiveness monitoring and decreasing unit (operatively connected to the first fluid processing unit); and processing the output vapor-gas, for forming processed vapor-gas product, by a second fluid processing unit (operatively connected to the vapor-gas explosiveness monitoring and decreasing unit).

According to some embodiments of the present invention, the method further includes receiving and transporting the processed vapor-gas product, by an output unit (operatively connected to the second fluid processing unit).

According to some embodiments of the present invention, the method further includes centrally process controlling each of the steps of the method, by a central process control unit (operatively connected to each of the fluid input unit, the first fluid processing unit, the vapor-gas explosiveness monitoring and decreasing unit, the second fluid processing unit, and optionally, the output unit).

According to another main aspect of some embodiments of the present invention, there is provided a method for monitoring and decreasing explosiveness of a vapor-gas, the method comprising: receiving and transporting the vapor-gas; measuring at least an indication of explosiveness level of the vapor-gas, wherein if the measurement of the vapor-gas exceeds a pre-determined threshold explosiveness level (PDTEL), then part of the vapor-gas is condensed, for forming a condensate, and an output vapor-gas whose explosiveness level is less than lower explosion limit (LEL) of the output vapor-gas; and receiving and transporting the output vapor-gas.

More specifically, in relation to main components of a corresponding unit (device), according to another main aspect of some embodiments of the present invention, there is provided a method for monitoring and decreasing explosiveness of a vapor-gas, the method comprising: receiving and transporting the vapor-gas, by a vapor-gas input assembly; measuring at least an indication of explosiveness level of the vapor-gas, wherein if the measurement of the vapor-gas exceeds a pre-determined threshold explosiveness level (PDTEL), then part of the vapor-gas is condensed, for forming a condensate, and an output vapor-gas whose explosiveness level is less than lower explosion limit (LEL) of the output vapor-gas, by a vapor-gas explosiveness level measuring mechanism (operatively connected to the vapor-gas input assembly); and receiving and transporting the output vapor-gas, by a vapor-gas output assembly (operatively connected to the vapor-gas explosiveness level measuring mechanism).

According to another main aspect of some embodiments of the present invention, there is provided a system for safely processing a fluid, comprising: a fluid input unit, suitable for receiving and transporting the fluid; a first fluid processing unit, suitable for being operatively connected to the fluid input unit, for receiving and processing the fluid, and for forming a processed fluid including a vapor-gas portion; a vapor-gas explosiveness monitoring and decreasing unit, suitable for being operatively connected to the first fluid processing unit, for receiving, and, for measuring at least an indication of explosiveness level of, the vapor-gas portion, wherein if the measurement of the vapor-gas portion exceeds a pre-determined threshold explosiveness level (PDTEL), then part of the vapor-gas portion is condensed, for forming a condensate, and an output vapor-gas whose explosiveness level is less than lower explosion limit (LEL) of the output vapor-gas; and a second fluid processing unit, suitable for being operatively connected to the vapor-gas explosiveness monitoring and processing unit, for receiving and processing the output vapor-gas, and for forming processed vapor-gas product.

According to some embodiments of the present invention, the system further includes an output unit, suitable for being operatively connected to the second fluid processing unit, for receiving and transporting the processed vapor-gas product.

According to some embodiments of the present invention, the system further includes a central process control unit, suitable for being operatively connected to each of the fluid input unit, the first fluid processing unit, the vapor-gas explosiveness monitoring and decreasing unit, the second fluid processing unit, and optionally, the output unit, for enabling central process control of each of these system units.

According to another main aspect of some embodiments of the present invention, there is provided a vapor-gas explosiveness monitoring and decreasing unit for monitoring and decreasing explosiveness of a vapor-gas, comprising: a vapor-gas input assembly, suitable for receiving and transporting the vapor-gas; a vapor-gas condensing device, suitable for being operatively connected to the vapor-gas input assembly, and for receiving and transporting the vapor-gas; a vapor-gas explosiveness level measuring mechanism, suitable for being operatively connected to the vapor-gas condensing device, and for measuring at least an indication of explosiveness level of the vapor-gas, wherein if the measurement of the vapor-gas exceeds a pre-determined threshold explosiveness level (PDTEL), then the vapor-gas condensing device condenses part of the vapor-gas for forming a condensate, and an output vapor-gas whose explosiveness level is less than lower explosion limit (LEL) of the output vapor-gas; and a vapor-gas output assembly, suitable for being operatively connected to the vapor-gas condensing device, for receiving and transporting the output vapor-gas.

According to some embodiments of the present invention, the pre-determined threshold explosiveness level (PDTEL) is equal to 75% (0.75) of the LEL (lower explosion limit) of the vapor-gas portion.

According to some embodiments of the present invention, the pre-determined threshold explosiveness level (PDTEL) is equal to 50% (0.50) of the LEL (lower explosion limit) of the vapor-gas portion.

According to some embodiments of the present invention, the pre-determined threshold explosiveness level (PDTEL) is equal to 25% (0.25) of the LEL (lower explosion limit) of the vapor-gas portion.

According to some embodiments of the present invention, measurement of the vapor-gas portion does not exceed the pre-determined threshold explosiveness level (PDTEL), then the vapor-gas portion is not condensed, for forming (non-condensed) output vapor-gas whose explosiveness level is less than the lower explosion limit (LEL) of the output vapor-gas.

According to some embodiments of the present invention, the vapor-gas portion is condensed by a vapor-gas condensing device.

According to some embodiments of the present invention, the vapor-gas condensing device is activated by a vapor-gas explosiveness level measuring mechanism.

According to some embodiments of the present invention, the measuring is performed by a vapor-gas explosiveness level measuring mechanism.

According to some embodiments of the present invention, the measuring is performed at a position or location downstream from a vapor-gas condensing device, at a time after the output vapor-gas exits a vapor-gas condensing device.

According to some embodiments of the present invention, the measuring is also performed at a position or location upstream from a vapor-gas output assembly, at a time before the output vapor-gas enters a vapor-gas output assembly.

According to some embodiments of the present invention, the measuring is first performed at a position or location downstream from a vapor-gas input assembly, at a time after the vapor-gas portion exits a vapor-gas input assembly.

According to some embodiments of the present invention, the measuring is also performed at a position or location upstream from a vapor-gas condensing device, at a time before the vapor-gas portion enters the vapor-gas condensing device.

According to some embodiments of the present invention, the measuring is also performed at a position or location downstream from the vapor-gas condensing device, at a time after the output vapor-gas exits the vapor-gas condensing device.

According to some embodiments of the present invention, processing of the output vapor-gas is performed by an oxidizer.

According to some embodiments of the present invention, the oxidizer is a thermal oxidizer.

According to some embodiments of the present invention, the thermal oxidizer is a regenerative thermal oxidizer.

Some embodiments of the present invention are implemented by performing steps or procedures, and sub-steps or sub-procedures, in a manner selected from the group consisting of manually, semi-automatically, fully automatically, and a combination thereof, involving use and operation of system units, system sub-units, devices, assemblies, sub-assemblies, mechanisms, structures, components, and elements, and, peripheral equipment, utilities, accessories, and materials. Moreover, according to actual steps or procedures, sub-steps or sub-procedures, system units, system sub-units, devices, assemblies, sub-assemblies, mechanisms, structures, components, and elements, and, peripheral equipment, utilities, accessories, and materials, used for implementing a particular embodiment of the disclosed invention, the steps or procedures, and sub-steps or sub-procedures, are performed by using hardware, software, or/and an integrated combination thereof, and the system units, sub-units, devices, assemblies, sub-assemblies, mechanisms, structures, components, and elements, and, peripheral equipment, utilities, accessories, and materials, operate by using hardware, software, or/and an integrated combination thereof.

For example, software used, via an operating system, for implementing some embodiments of the present invention can include operatively interfaced, integrated, connected, or/and functioning written or/and printed data, in the form of software programs, software routines, software sub-routines, software symbolic languages, software code, software instructions or protocols, software algorithms, or a combination thereof. For example, hardware used for implementing some embodiments of the present invention can include operatively interfaced, integrated, connected, or/and functioning electrical, electronic or/and electromechanical system units, sub-units, devices, assemblies, sub-assemblies, mechanisms, structures, components, and elements, and, peripheral equipment, utilities, accessories, and materials, which may include one or more computer chips, integrated circuits, electronic circuits, electronic sub-circuits, hard-wired electrical circuits, or a combination thereof, involving digital or/and analog operations. Some embodiments of the present invention can be implemented by using an integrated combination of the just described exemplary software and hardware.

In exemplary embodiments of the present invention, steps or procedures, and sub-steps or sub-procedures, can be performed by a data processor, such as a computing platform, for executing a plurality of instructions. Optionally, the data processor includes volatile memory for storing instructions or/and data, or/and includes non-volatile storage, for example, a magnetic hard-disk or/and removable media, for storing instructions or/and data. Optionally, exemplary embodiments of the present invention include a network connection. Optionally, exemplary embodiments of the present invention include a display device and a user input device, such as a keyboard or/and 'mouse'.

BRIEF DESCRIPTION OF THE DRAWINGS

Some embodiments of the present invention are herein described, by way of example only, with reference to the accompanying drawings. With specific reference now to the drawings in detail, it is stressed that the particulars shown are by way of example and for purposes of illustrative description of some embodiments of the present invention. In this regard, the description taken together with the accompanying drawings make apparent to those skilled in the art how the embodiments of the present invention may be practiced.

In the drawings:

FIG. 1 is a (block-type) flow diagram of an exemplary embodiment of the main steps (procedures) of the method ('the safe fluid processing method') for safely processing a fluid via monitoring and decreasing explosiveness of vapor-gas species formed therefrom, or contained therein, in accordance with the present invention;

FIG. 5 is a schematic diagram illustrating an exemplary embodiment of the main components, and additional fluid processing components, of a system for safely processing (decontaminating, purifying) a contaminated (liquid) fluid, such as contaminated water (wastewater), via monitoring and decreasing explosiveness of vapor-gas species formed therefrom, which can be used for implementing the exemplary embodiment of the method presented in FIG. 1, in accordance with the present invention; and FIG. 6 is a schematic diagram illustrating an exemplary embodiment of the main components, and additional fluid processing components, of a system for safely processing (decontaminating, purifying) a contaminated (vapor-gas) fluid, such as contaminated air (waste exhaust), via monitoring and decreasing explosiveness of vapor-gas species contained therein, which can be used for implementing the exemplary embodiment of the method presented in FIG. 1, in accordance with the present invention.

DESCRIPTION OF SPECIFIC EMBODIMENTS OF THE INVENTION

Figure 2:
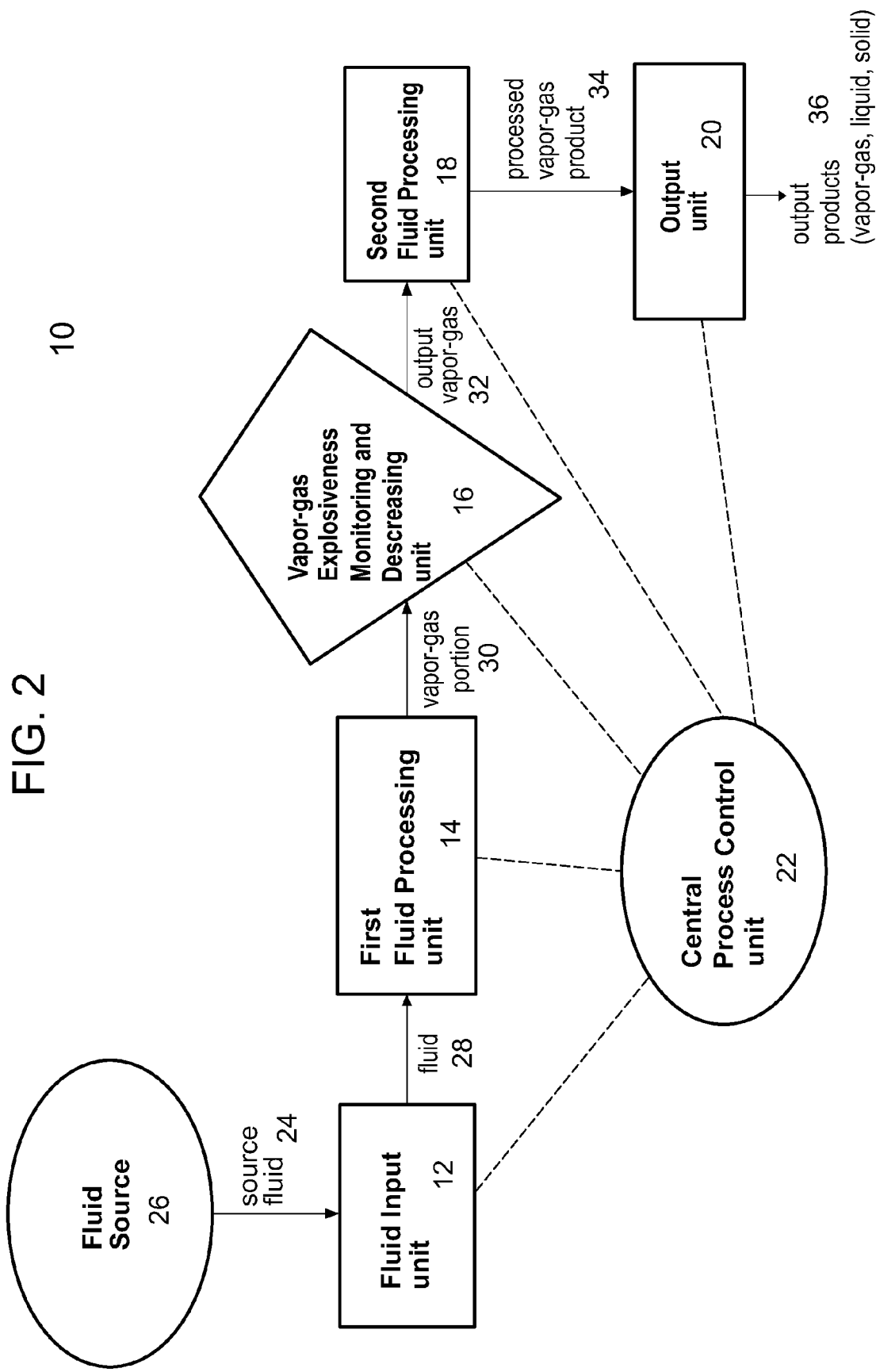
FIG. 2 is a schematic diagram illustrating an exemplary embodiment of the main components of the system ('the safe fluid processing system') for safely processing a fluid via monitoring and decreasing explosiveness of vapor-gas species formed therefrom, or contained therein, which can be used for implementing the exemplary embodiment of the method presented in FIG. 1, in accordance with the present invention.

The present invention, in some embodiments thereof, relates to safely processing a (liquid or vapor-gas) fluid, where the processing involves vapor-gas species that are explosive, and more particularly, but not exclusively, to safely processing a fluid via monitoring and decreasing explosiveness of vapor-gas species formed therefrom, or contained therein. The present invention is generally applicable to essentially any type or kind, and scale (size), of processing of essentially any type or kind of liquid fluid or vapor-gas fluid, where processing of the fluid involves explosive (combustible) vapor-gas species. Some embodiments of the present invention are generally applicable to safely processing a liquid or vapor-gas fluid which involves explosive (combustible) vapor-gas species being volatile (combustible) compounds, such as volatile (combustible) organic or/and inorganic compounds. In exemplary embodiments of the present invention, the fluid is a liquid being contaminated water, such as industrial wastewater, contaminated with volatile (combustible) organic or/and inorganic compounds, and the processing is based on safely removing the water contaminants from (i.e., decontaminating or purifying) the contaminated water (wastewater). In other exemplary embodiments of the present invention, the fluid is a vapor-gas being contaminated air, such as industrial waste exhaust, contaminated with volatile (combustible) organic or/and inorganic compounds, and the processing is based on safely removing the air contaminants from (i.e., decontaminating or purifying) the contaminated air (waste exhaust).

A main aspect of some embodiments of the present invention is provision of a method for safely processing a fluid, the method including the following main steps or procedures, and, components and functionalities thereof: (a) receiving and transporting the fluid, by a fluid input unit; (b) processing the fluid, for forming a processed fluid including a vapor-gas portion, by a first fluid processing unit (operatively connected to the fluid input unit); (c) measuring at least an indication of explosiveness level of the vapor-gas portion, wherein if the measurement of the vapor-gas portion exceeds a pre-determined threshold explosiveness level (PDTEL), then part of the vapor-gas portion is condensed, for forming a condensate, and an output vapor-gas whose explosiveness level is less than lower explosion limit (LEL) of the output vapor-gas, by a vapor-gas explosiveness monitoring and decreasing unit (operatively connected to the first fluid processing unit); and (d) processing the output vapor-gas, for forming processed vapor-gas product, by a second fluid processing unit (operatively connected to the vapor-gas explosiveness monitoring and decreasing unit).

Some embodiments of the method further include: receiving and transporting the processed vapor-gas product, by an output unit (operatively connected to the second fluid processing unit).

Some embodiments of the method further include: centrally process controlling each of the steps of the method, by a central process control unit (operatively connected to each of the fluid input unit, the first fluid processing unit, the vapor-gas explosiveness monitoring and decreasing unit, the second fluid processing unit, and optionally, the output unit).

By way of main step (c) being a sub-combination of the method, therefore, the present invention, in some embodiments thereof, also features a method for monitoring and decreasing explosiveness of a vapor-gas. Accordingly, another main aspect of some embodiments of the present invention is provision of a method for monitoring and decreasing explosiveness of a vapor-gas, the method including the following main steps or procedures, and, components and functionalities thereof: (a) receiving and transporting the vapor-gas, by a vapor-gas input assembly; (b) measuring at least an indication of explosiveness level of the vapor-gas, wherein if the measurement of the vapor-gas exceeds a pre-determined threshold explosiveness level (PDTEL), then part of the vapor-gas is condensed, for forming a condensate, and an output vapor-gas whose explosiveness level is less than lower explosion limit (LEL) of the output vapor-gas, by a vapor-gas explosiveness level measuring mechanism (operatively connected to the vapor-gas input assembly); and receiving and transporting the output vapor-gas, by a vapor-gas output assembly (operatively connected to the vapor-gas explosiveness level measuring mechanism).

Another main aspect of some embodiments of the present invention is provision of a corresponding system for safely processing a fluid, the system including the following main components and functionalities thereof: (a) a fluid input unit, configured for receiving and transporting the fluid; a first fluid processing unit, configured for being operatively connected to the fluid input unit, for receiving and processing the fluid, and for forming a processed fluid including a vapor-gas portion; (b) a vapor-gas explosiveness monitoring and decreasing unit, configured for being operatively connected to the first fluid processing unit, for receiving, and, for measuring at least an indication of explosiveness level of, the vapor-gas portion, wherein if the measurement of the vapor-gas portion exceeds a pre-determined threshold explosiveness level (PDTEL), then part of the vapor-gas portion is condensed, for forming a condensate, and an output vapor-gas whose explosiveness level is less than lower explosion limit (LEL) of the output vapor-gas; and (c) a second fluid processing unit, configured for being operatively connected to the vapor-gas explosiveness monitoring and processing unit, for receiving and processing the output vapor-gas, and for forming processed vapor-gas product.

Some embodiments of the system further include: (d) an output unit, configured for being operatively connected to the second fluid processing unit, for receiving and transporting the processed vapor-gas product.

Some embodiments of the system further include: (e) a central process control unit, configured for being operatively connected to each of the fluid input unit, the first fluid processing unit, the vapor-gas explosiveness monitoring and decreasing unit, the second fluid processing unit, and optionally, the output unit, for enabling central process control of each of these system units.

By way of the vapor-gas explosiveness monitoring and processing unit being a sub-combination of the system, therefore, the present invention, in some embodiments thereof, also features a device, corresponding to the vapor-gas explosiveness monitoring and processing unit, for monitoring and decreasing explosiveness of a vapor-gas. Accordingly, another main aspect of some embodiments of the present invention is provision of a vapor-gas explosiveness monitoring and processing unit, for monitoring and decreasing explosiveness of a vapor-gas. The vapor-gas explosiveness monitoring and processing unit, in some embodiments, includes the following main components and functionalities thereof: (a) a vapor-gas input assembly, configured for receiving and transporting the vapor-gas; (b) a vapor-gas condensing device, configured for being operatively connected to the vapor-gas input assembly, and for receiving and transporting the vapor-gas; (c) a vapor-gas explosiveness level measuring mechanism, configured for being operatively connected to the vapor-gas condensing device, and for measuring at least an indication of explosiveness level of the vapor-gas, wherein if the measurement of the vapor-gas exceeds a pre-determined threshold explosiveness level (PDTEL), then the vapor-gas condensing device condenses part of the vapor-gas for forming a condensate, and an output vapor-gas whose explosiveness level is less than lower explosion limit (LEL) of the output vapor-gas; and (d) a vapor-gas output assembly, configured for being operatively connected to the vapor-gas condensing device, for receiving and transporting the output vapor-gas.

In some embodiments of the present invention, the pre-determined threshold explosiveness level (PDTEL) is equal to 75% (0.75) of the LEL (Lower Explosion Limit) of the vapor-gas. In some embodiments of the present invention, the pre-determined threshold explosiveness level (PDTEL) is equal to 50% (0.50) of the LEL (Lower Explosion Limit) of the vapor-gas. In some embodiments of the present invention, the pre-determined threshold explosiveness level (PDTEL) is equal to 25% (0.25) of the LEL (Lower Explosion Limit) of the vapor-gas.

Based on the above stated main aspects, some embodiments of the present invention include several special technical features, and, aspects of novelty and inventiveness over prior art teachings in the relevant fields and arts of fluid processing, in general, and of safely processing a (liquid or vapor-gas) fluid, in particular, where the fluid processing involves vapor-gas species that are explosive.

It is to be understood that the present invention is not limited in its application to the details of the order or sequence, and number, of steps or procedures, and sub-steps or sub-procedures, of operation or implementation of some embodiments of the method/process, or to the details of type, composition, construction, arrangement, order, and number, of the system units, system sub-units, devices, assemblies, sub-assemblies, mechanisms, structures, components, elements, and configurations, and, peripheral equipment, utilities, accessories, chemical reagents, and materials, of some embodiments of the system and unit (device), set forth in the following illustrative description, accompanying drawings, and examples, unless otherwise specifically stated herein.

For example, in the following, in order to illustrate implementation of some embodiments of the present invention, there is provided illustrative description of an exemplary (specific) embodiment of the main components, and additional fluid processing components, of a system for safely processing (decontaminating, purifying) a contaminated (liquid) fluid, such as contaminated water (wastewater), via monitoring and decreasing explosiveness of vapor-gas species formed therefrom, which can be used for implementing the exemplary embodiment of the (generalized) method, in accordance with the present invention. Additionally, for example, in the following, in order to illustrate implementation of other embodiments of the present invention, there is also provided illustrative description of an exemplary (specific) embodiment of the main components, and additional fluid processing components, of a system for safely processing (decontaminating, purifying) a contaminated (vapor-gas) fluid, such as contaminated air (waste exhaust), via monitoring and decreasing explosiveness of vapor-gas species contained therein, which can be used for implementing the exemplary embodiment of the (generalized) method, in accordance with the present invention.

It is to be fully understood that some embodiments of the present invention are generally applicable to essentially any type or kind, and scale (size), of processing of essentially any type or kind of liquid fluid or vapor-gas fluid, where processing of the fluid involves essentially any type or kind of explosive (combustible) vapor-gas species. It is also to be fully understood that some embodiments of the present invention are generally applicable to safely processing a liquid or vapor-gas fluid which involves explosive (combustible) vapor-gas species being essentially any type or kind of volatile (combustible) compounds, such as volatile (combustible) organic or/and inorganic compounds. Accordingly, the present invention can be practiced or implemented according to various alternative embodiments and in various alternative ways.

It is also to be understood that all technical and scientific words, terms, or/and phrases, used herein throughout the present disclosure have either the identical or similar meaning as commonly understood by one of ordinary skill in the art to which this invention belongs, unless otherwise specifically defined or stated herein. Phraseology, terminology, and, notation, employed herein throughout the present disclosure are for the purpose of description and should not be regarded as limiting. For example, in the illustrative description of some embodiments of the present invention, there are general and specific references to, and uses of, the key technical terms and phrases: 'processing', 'fluid', 'liquid', 'vapor-gas', 'explosive', 'explosiveness level', and 'explosion limit (LEL)', among various other key technical terms and phrases, in order to illustrate implementation of some embodiments of the present invention.

Moreover, all technical and scientific words, terms, or/and phrases, introduced, defined, described, or/and exemplified, in the above Field and Background sections, are equally or similarly applicable in the illustrative description of the embodiments, examples, and appended claims, of the present invention. Immediately following are selected definitions and exemplary usages of words, terms, or/and phrases, which are used throughout the illustrative description of embodiments, examples, and appended claims, of the present invention, and are especially relevant for understanding thereof.

Each of the following terms written in singular grammatical form: 'a', 'an', and 'the', as used herein, may also refer to, and encompass, a plurality of the stated entity or object, unless otherwise specifically defined or stated herein, or, unless the context clearly dictates otherwise. For example, the phrases 'a unit', 'a device', 'an assembly', 'a mechanism', 'a component', and 'an element', as used herein, may also refer to, and encompass, a plurality of units, a plurality of devices, a plurality of assemblies, a plurality of mechanisms, a plurality of components, and a plurality of elements, respectively. Additionally, for example, the phrase 'a compound' may also refer to, and encompass, a plurality of compounds, or/and mixtures thereof. Additionally, for example, the phrase 'a vapor-gas species' may also refer to, and encompass, a plurality of vapor-gas species, or/and mixtures thereof.

Each of the following terms: 'includes', 'including', 'has', 'having', 'comprises', and 'comprising', and, their linguistic/grammatical variants, derivatives, or/and conjugates, as used herein, means 'including, but not limited to'.

The phrase 'operatively connected', as used herein, equivalently refers to the corresponding synonymous phrases 'operatively joined', and 'operatively attached', where the operative connection, operative joint, or operative attachment, is according to a physical, or/and electrical, or/and electronic, or/and mechanical, or/and electro-mechanical, manner or nature, involving various types and kinds of hardware or/and software equipment and components.

The term 'processing', as used herein, refers to putting a (liquid or vapor-gas) fluid through the steps of a prescribed method, process, or procedure. The term 'processing', as used herein, also refers to preparing, treating, or converting, by subjecting a (liquid or vapor-gas) fluid to the steps of a prescribed method, process, or procedure. Exemplary specific types or kinds of fluid processing, which are suitable for implementing some embodiments of the present invention, are: decontaminating, purifying, treating, reacting, and synthesizing. Moreover, any of these specific types or kinds of fluid processing may include, or involve, specific types or kinds of processing that are based on destruction/destructing, removal/removing, of an entire (liquid or vapor-gas) fluid, or of components or species of a (liquid or vapor-gas) fluid. Moreover, any of these specific types or kinds of fluid processing may include, or involve, more specific types or kinds of processing that are based on stripping, combustion, oxidation, condensation, distillation, vaporization, or/and compression, of an entire (liquid or vapor-gas) fluid, or of components or species of a (liquid or vapor-gas) fluid. Moreover, exemplary specific types or kinds of processing based on oxidation, may include, or involve, thermal oxidation, or/and thermal-catalytic oxidation The term 'fluid', as used herein, refers to a state of matter, such as liquid, vapor, or gas, in which the component particles (generally molecules) can move past one another. More technically, the term 'fluid', as used herein, refers to a substance that continually deforms (flows) under an applied shear stress. All liquids, vapors, and gases are considered fluids.

The term 'liquid', as used herein, refers to the state of matter in which a substance exhibits a characteristic readiness to flow, little or no tendency to disperse, and relatively high incompressibility. More technically, the term 'liquid', as used herein, refers to one of the principal states of matter. A liquid is a fluid that has the particles loose and can freely form a distinct surface at the boundaries of its bulk material.

The term 'gas', as used herein, refers to one of the phases of matter; a substance in the gaseous state; a compressible fluid phase. More technically, the term 'gas', as used herein, refers to the state of matter distinguished from the solid and liquid states by relatively low density and viscosity, relatively great expansion and contraction with changes in pressure and temperature, the ability to diffuse readily, and the spontaneous tendency to become distributed uniformly throughout any container.

The term 'vapor', as used herein, refers to barely visible or cloudy diffused matter, such as mist, fumes, or smoke, suspended in the air. More technically, the term 'vapor', as used herein, refers to the gaseous state of a substance that is liquid or solid under ordinary conditions, and refers to the state of a substance that exists below its critical temperature and that may be liquefied (or solidified) by application of sufficient pressure. Additionally, a vapor is considered a substance in the gas phase at a temperature lower than its critical temperature, whereby the vapor can be condensed to a liquid (or solid) by increasing its pressure, without reducing the temperature.

The term 'vapor-gas', as used herein, refers to any one of the following: gas, vapor, or a mixture of gas and vapor. The term 'vapor-gas' is generally, and collectively, used with respect to gas or/and vapor types, states, or/and phases of matter, since an important aspect of some embodiments of the present invention relates to those types or kinds of a 'vapor-gas' having the particular physicochemical property, characteristic, and behavior of being 'explosive (combustible, flammable, ignitable, burnable)', and not to those particular physicochemical properties, characteristics, or behavior, which may be relevant for technically distinguishing between a gas and a vapor, or mixtures thereof. The phrase 'vapor-gas species', as used herein, generally refers to any type or kind of a vapor-gas type, state, or/and phase, of matter, or, to any type or kind of component thereof. Such a component of the vapor-gas may be a single or individual pure substance or material of matter (such as an element, or a compound), or may be a combination of single or individual pure substances or materials of matter (such as a compound), or may be a mixture of single or individual pure substances or materials of matter (such as a mixture of elements, a mixture of compounds, or a mixture of elements and compounds).

The terms 'explosive', as used herein, refers to descriptive characterization of a substance or material of matter, particularly, a vapor-gas species, that has physicochemical properties, characteristics, and behavior, relating to or having the nature of tendency (potential) to explode or cause to explode, or capability to explode or cause to explode. The term 'explosive', as used herein, also refers to descriptive characterization of a substance or material of matter, particularly, a vapor-gas species, that may undergo, or undergoes, a rapid chemical change (with the production of gas) on being heated or struck.

The term 'explosive', as used herein, also refers to descriptive characterization of a substance or material of matter, particularly, a vapor-gas species, that undergoes decomposition or combustion with great rapidity, evolving much heat and producing a large volume of gas. The term 'explosive' can be considered synonymous with the term 'combustible', 'flammable', or 'ignitable'.

The term 'explosiveness', as used herein, refers to the state or condition of a substance or material of matter, particularly, a vapor-gas species, that is explosive (as defined above).

The phrase 'explosiveness level' (EL), as used herein, refers to the level (i.e., extent or magnitude) of explosiveness of a substance or material of matter, particularly, a vapor-gas species.

The phrase 'explosion limit', as used herein, refers to the proportion of combustible gases (vapors, gases) in a mixture, between which limits this mixture is explosive, combustible, or flammable. Gas (vapor, vapor-gas) mixtures consisting of combustible, oxidizing, and inert gases (vapors) are only explosive, combustible, or flammable under certain conditions. The lower explosion limit (LEL) describes the leanest mixture that is still explosive, combustible, or flammable, i.e. the mixture with the smallest fraction of explosive, combustible, or flammable, gas (vapor, vapor-gas), while the upper explosion limit (UEL) gives the richest explosive, combustible, or flammable, mixture. The lower explosion limit (LEL), also known as the lower flammability limit (LFL), of a mixture of several combustible gases (vapor-gases) can be calculated using Le Chatelier's mixing rule for explosive (combustible) volume fractions $x_i$:

$$LFL_{mix} = \frac{1}{\sum_i \frac{x_i}{LFL_i}}$$

In view of the above selected definitions and exemplary usages of words, terms, or/and phrases, which are used throughout the illustrative description of embodiments, examples, and appended claims, of the present invention, it is to be fully understood that some embodiments of the present invention are generally applicable to essentially any type or kind, and scale (size), of processing of essentially any type or kind of liquid fluid or vapor-gas fluid, where processing of the fluid involves essentially any type or kind of explosive (combustible) vapor-gas species, and, it is also to be fully understood that some embodiments of the present invention are generally applicable to safely processing a liquid or vapor-gas fluid which involves explosive (combustible) vapor-gas species being essentially any type or kind of volatile (combustible) compounds, such as volatile (combustible) organic or/and inorganic compounds.

The term 'about', as used herein, refers to ±10% of the stated numerical value.

The phrase 'room temperature', as used herein, refers to a temperature in a range of between about 20° C. and about 25° C.

Throughout the illustrative description of the embodiments, the examples, and the appended claims, of the present invention, a numerical value of a parameter, feature, object, or dimension, may be stated or described in terms of a numerical range format. It is to be fully understood that the stated numerical range format is provided for illustrating implementation of some embodiments of the present invention, and is not to be understood or construed as inflexibly limiting the scope of some embodiments of the present invention.

Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', is considered equivalent to, and meaning the same as, the phrase 'room temperature refers to a temperature in a range of from about 20° C. to about 25° C.'.

Steps or procedures, sub-steps or sub-procedures, and, equipment and materials, system units, system sub-units, devices, assemblies, sub-assemblies, mechanisms, structures, components, elements, and configurations, and, peripheral equipment, utilities, accessories, chemical reagents, and materials, as well as operation and implementation, of exemplary embodiments, alternative embodiments, specific configurations, and, additional and optional aspects, characteristics, or features, thereof, according to the present invention, are better understood with reference to the following illustrative description and accompanying drawings. Throughout the following illustrative description and accompanying drawings, same reference notation and terminology (i.e., numbers, letters, or/and symbols), refer to same system units, system sub-units, devices, assemblies, sub-assemblies, mechanisms, structures, components, elements, and configurations, and, peripheral equipment, utilities, chemical reagents, accessories, and materials, components, elements, or/and parameters.

According to a main aspect of some embodiments of the present invention, there is provision of a method for safely processing a fluid, herein, also referred to as 'the safe fluid processing method'. According to another main aspect of some embodiments of the present invention, there is provision of a corresponding system for safely processing a fluid, herein, also referred to as 'the safe fluid processing system'. According to another main aspect of some embodiments of the present invention, there is provision of a method for monitoring and decreasing explosiveness of a vapor-gas. According to another main aspect of some embodiments of the present invention, there is provision of a corresponding vapor-gas explosiveness monitoring and processing unit, for monitoring and decreasing explosiveness of a vapor-gas.

Referring now to the drawings, FIG. 1 is a (block-type) flow diagram of an exemplary embodiment of the main steps (procedures) of the method ('the safe fluid processing method') for safely processing a fluid via monitoring and decreasing explosiveness of vapor-gas species formed therefrom, or contained therein, in accordance with the present invention. In FIG. 1, each main step (procedure) of the method for safely processing a fluid is enclosed inside a separate block (frame) which is assigned a reference number. Accordingly, main steps (procedures) (a), (b), (c), and (d), are enclosed inside of blocks (frames) 2, 4, 6, and 8, respectively. FIG. 2 is a schematic diagram illustrating an exemplary embodiment of the main components of the system ('the safe fluid processing system') for safely processing a fluid via monitoring and decreasing explosiveness of vapor-gas species formed therefrom, or contained therein, which can be used for implementing the exemplary embodiment of the method for safely processing a fluid (as presented in FIG. 1), in accordance with the present invention.

Some embodiments of the method for safely processing a fluid via monitoring and decreasing explosiveness of vapor-gas species formed therefrom, or contained therein, in accordance with the present invention, are implemented by appropriately designing, configuring, constructing, and operating, a corresponding system, such as safe fluid processing system 10 shown in FIG. 2, for performing main Steps (a), (b), (c), and (d), shown in blocks (frames) 2, 4, 6, and 8, respectively, in FIG. 1, and various sub-steps thereof. For performing main steps (a), (b), (c), and (d), of some embodiments of the safe fluid processing method, safe fluid processing system 10 includes the main components of: a fluid input unit 12, a first fluid processing unit 14, a vapor-gas explosiveness monitoring and decreasing unit 16, and a second fluid processing unit 18. Some embodiments of the safe fluid processing method further include: receiving and transporting the processed vapor-gas product, by an output unit 20. Some embodiments of the safe fluid processing method further include: centrally process controlling each of the steps of the method, by a central process control unit 22.

Some embodiments of safe fluid processing system 10 are appropriately designed, constructed, and operative, such that some embodiments of the safe fluid processing method are implemented according to any of a variety of different specific modes of real time or near real time, off-line, on-line, in-line, continuous, or discontinuous (batch, or staggered), processing of a (liquid or vapor-gas) fluid (herein, referred to as source fluid 24 supplied by, or obtained from, a fluid source 26. Relevant structure and function (operation) of each main component (and components thereof), and synchronized operation of the combination of the main components (and components thereof), of some embodiments of safe fluid processing system 10 are illustratively described hereinbelow in the context of illustratively describing the main steps (procedures) of some embodiments of the safe fluid processing method.

With reference to FIG. 1, along with reference to FIG. 2, some embodiments of a method for safely processing a fluid, include the following main steps or procedures, and, components and functionalities thereof: (a) (block 2, FIG. 1) receiving and transporting the fluid, for example, source fluid 24 (supplied by, or obtained from, a fluid source 26), by fluid input unit 12 (operatively connected to fluid source 26); (b) (block 4, FIG. 1) processing the fluid (in FIG. 2, referred to as fluid 28, corresponding to source fluid 24 having been subjected to any type or kind, and number, of pre-treatment steps (procedures)), for forming a processed fluid including a vapor-gas portion 30, by first fluid processing unit 14 (operatively connected to fluid input unit 12); (c) (block 6, FIG. 1) measuring at least an indication of explosiveness level of vapor-gas portion 30, wherein if the measurement of vapor-gas portion 30 exceeds a pre-determined threshold explosiveness level (PDTEL), then part of vapor-gas portion 30 is condensed, for forming a condensate, and an output vapor-gas 32 whose explosiveness level is less than lower explosion limit (LEL) of output vapor-gas 32, by vapor-gas explosiveness monitoring and decreasing unit 16 (operatively connected to first fluid processing unit 14); and (d) (block 8, FIG. 1) processing output vapor-gas 32, for forming processed vapor-gas product 34, by second fluid processing unit 18 (operatively connected to vapor-gas explosiveness monitoring and decreasing unit 16).

Some embodiments of the safe fluid processing method further include: receiving and transporting processed vapor-gas product 34, by output unit 20 (operatively connected to second fluid processing unit 18). Processed vapor-gas product 34 is transported out of output unit 20 in the form of (vapor-gas, liquid, or/and solid) output products 36, for disposal, storage, or/and additional processing.

Some embodiments of the safe fluid processing method further include: centrally process controlling each of the steps of the method, by central process control unit 22 (operatively connected to each of fluid input unit 12, first fluid processing unit 14, vapor-gas explosiveness monitoring and decreasing unit 16, second fluid processing unit 18, and optionally, output unit 20).

Similarly, with reference to FIG. 2, along with reference to FIG. 1, some embodiments of a corresponding system (safe fluid processing system 10) for safely processing a fluid, for example, source fluid 24 (supplied by, or obtained from, fluid source 26), include the following main components and functionalities thereof: fluid input unit 12, configured for receiving and transporting source fluid 24 (block 2, FIG. 1); first fluid processing unit 14, configured for being operatively connected to fluid input unit 12, for receiving and processing fluid 26, and for forming a processed fluid including a vapor-gas portion 30 (block 4, FIG. 1); vapor-gas explosiveness monitoring and decreasing unit 16, configured for being operatively connected to first fluid processing unit 14, for receiving, and, for measuring at least an indication of explosiveness level of, vapor-gas portion 30, wherein if the measurement of vapor-gas portion 30 exceeds a pre-determined threshold explosiveness level (PDTEL), then part of vapor-gas portion 30 is condensed, for forming a condensate, and an output vapor-gas 32 whose explosiveness level is less than lower explosion limit (LEL) of output vapor-gas 32 (block 6, FIG. 1); and second fluid processing unit 18, configured for being operatively connected to vapor-gas explosiveness monitoring and processing unit 16, for receiving and processing output vapor-gas 32, and for forming processed vapor-gas product 34 (block 8, FIG. 1).

Some embodiments of the safe fluid processing system further include: output unit 20, configured for being operatively connected to second fluid processing unit 18, for receiving and transporting processed vapor-gas product 34. Processed vapor-gas product 34 is transported out of output unit 20 in the form of (vapor-gas, liquid, or/and solid) output products 36, for disposal, storage, or/and additional processing.

Some embodiments of the safe fluid processing system further include: central process control unit 22, configured for being operatively connected to each of fluid input unit 12, first fluid processing unit 14, vapor-gas explosiveness monitoring and decreasing unit 16, second fluid processing unit 18, and optionally, output unit 20, for enabling central process control of each of these system units.

In some embodiments of a method for safely processing a fluid, main step (c) (block 6, FIG. 1), measuring at least an indication of explosiveness level of vapor-gas portion 30, wherein if the measurement of vapor-gas portion 30 exceeds a pre-determined threshold explosiveness level (PDTEL), then part of vapor-gas portion 30 is condensed, for forming a condensate, and an output vapor-gas 32 whose explosiveness level is less than lower explosion limit (LEL) of output vapor-gas 32, by vapor-gas explosiveness monitoring and decreasing unit 16 (FIG. 2), corresponds to a sub-combination of the overall safe fluid processing method. Therefore, the present invention, in some embodiments thereof, also features a method for monitoring and decreasing explosiveness of a vapor-gas.

Figure 3:
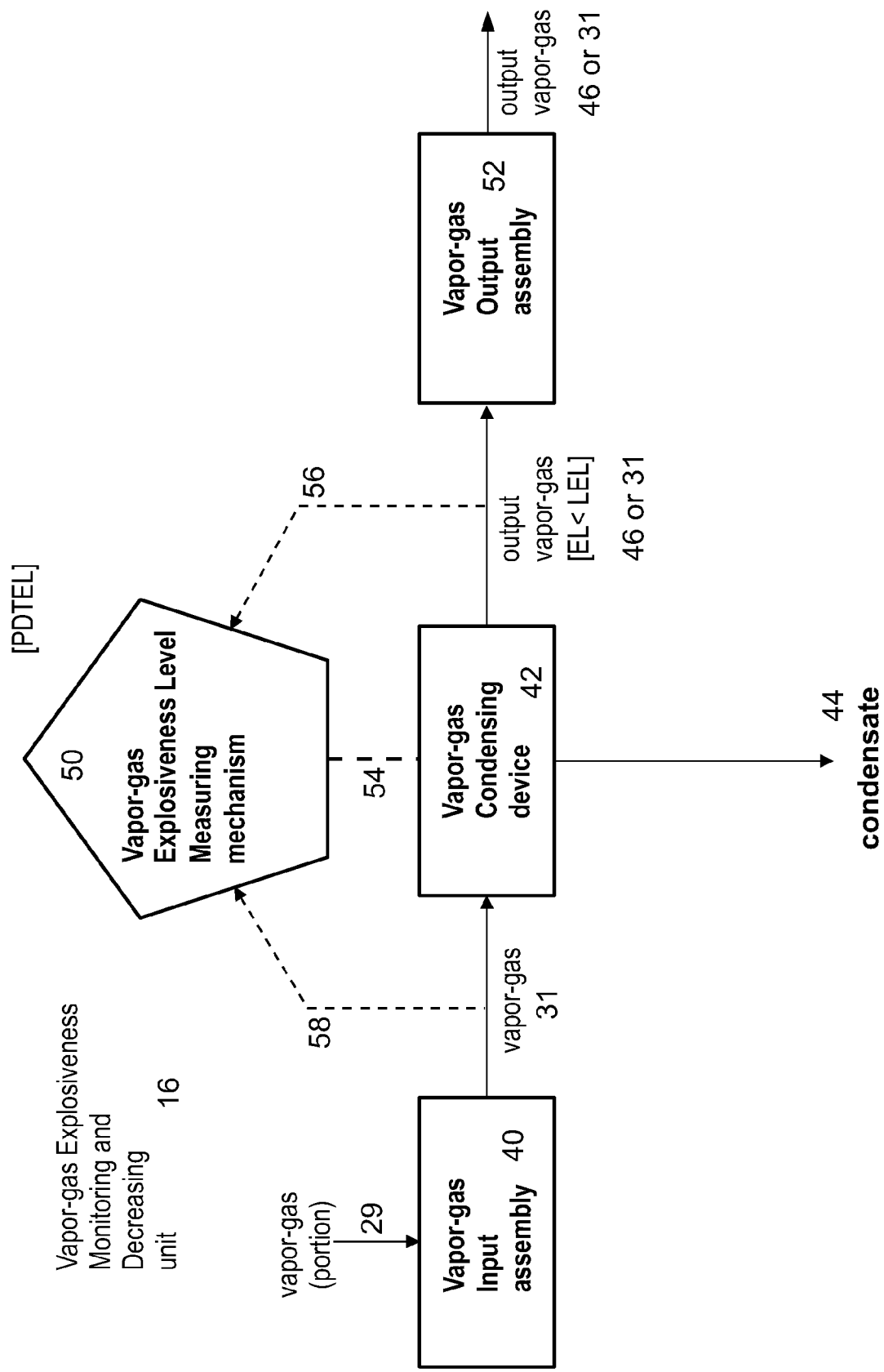
FIG. 3 is a schematic diagram illustrating an exemplary embodiment of the main components of the vapor-gas explosiveness monitoring and decreasing unit, included in the exemplary embodiment of the system illustrated in FIG. 2, in accordance with the present invention.

FIG. 3 is a schematic diagram illustrating an exemplary embodiment of the main components of vapor-gas explosiveness monitoring and decreasing unit 16, included in the exemplary embodiment of safe fluid processing system 10 illustrated in FIG. 2. With reference to FIG. 3, some embodiments of the method for monitoring and decreasing explosiveness of a vapor-gas include the following main steps or procedures, and, components and functionalities thereof: receiving and transporting the vapor-gas (for example, in FIG. 3 referred to as vapor-gas (portion) 29, corresponding to either vapor-gas portion 30 referenced in FIG. 2, or corresponding to a different vapor-gas fed into vapor-gas explosiveness monitoring and decreasing unit 16), by a vapor-gas input assembly 40; measuring at least an indication of explosiveness level (EL) of the vapor-gas (in FIG. 3, referred to as vapor-gas 31, corresponding to vapor-gas (portion) 29 having been subjected to any type or kind, and number, of pre-treatment steps (procedures)), wherein if the measurement (EL) of vapor-gas 31 exceeds a pre-determined threshold explosiveness level (PDTEL), then part of vapor-gas 31 is condensed (for example, via a vapor-gas condensing device 42), for forming a condensate 44, and an output vapor-gas 46 whose explosiveness level (EL) is less than lower explosion limit (LEL) of output vapor-gas 46, by a vapor-gas explosiveness level measuring mechanism 50 (operatively connected to vapor-gas input assembly 40, for example, via vapor-gas condensing device 42); and receiving and transporting output vapor-gas 46, by a vapor-gas output assembly 52 (operatively connected to vapor-gas explosiveness level measuring mechanism 50, for example, via vapor-gas condensing device 42).

According to the preceding embodiment, vapor-gas condensing device 42, which is operatively connected to vapor-gas input assembly 40, to vapor-gas explosiveness level measuring mechanism 50, and to vapor-gas output assembly 52, is activated (in FIG. 3, indicated by the bold dashed line 54 extending between, and connecting, vapor-gas condensing device 42 and vapor-gas explosiveness level measuring mechanism 50) by vapor-gas explosiveness level measuring mechanism 50, for condensing part of vapor-gas 31, for forming a condensate 44, and output vapor-gas 46 whose explosiveness level (EL) is less than lower explosion limit (LEL) of output vapor-gas 46.

Alternatively, if the measurement (EL) of vapor-gas 31 'does not' exceed the pre-determined threshold explosiveness level (PDTEL), then vapor-gas 31 'is not' condensed (for example, by passing through vapor-gas condensing device 42 according to a non-condensing configuration or mode of operation), for forming (non-condensed) output vapor-gas 31 whose explosiveness level (EL) is less than lower explosion limit (LEL) of output vapor-gas 31, by vapor-gas explosiveness level measuring mechanism 50 (operatively connected to vapor-gas input assembly 40); and receiving and transporting output vapor-gas 31, by vapor-gas output assembly 52 (operatively connected to vapor-gas explosiveness level measuring mechanism 50).

As illustrated in FIG. 3, measuring the explosiveness level (EL) of vapor-gas 31 can be performed according to either one of two different possible alternative modes. According to a first mode, as indicated in FIG. 3 by dashed arrow 56, measuring at least an indication of the explosiveness level (EL) of vapor-gas 31 (or 46) is performed at a position or location downstream from (i.e., after) vapor-gas condensing device 42, at a time after vapor-gas 31 (or 46) exits vapor-gas condensing device 42, but at a position or location upstream from (i.e., before) vapor-gas output assembly 52, at a time before vapor-gas 31 (or 46) enters vapor-gas output assembly 52. According to a second mode, measuring at least an indication of the explosiveness level (EL) of vapor-gas 31 is first performed at a position or location downstream from (i.e., after) vapor-gas input assembly 40, at a time after vapor-gas 31 exits vapor-gas input assembly 40, but at a position or location upstream from (i.e., before) vapor-gas condensing device 42, at a time before vapor-gas 31 enters vapor-gas condensing device 42, as indicated in FIG. 3 by dashed arrow 58, AND is also performed at a position or location downstream from (i.e., after) vapor-gas condensing device 42, at a time after vapor-gas 31 (or 46) exits vapor-gas condensing device 42, but at a position or location upstream from (i.e., before) vapor-gas output assembly 52, at a time before vapor-gas 31 (or 46) enters vapor-gas output assembly 52 (dashed arrow 56).

According to either mode, measuring at least an indication of the explosiveness level (EL) of vapor-gas 31 (or 46) is performed at a position or location downstream from (i.e., after) vapor-gas condensing device 42, at a time after vapor-gas 31 (or 46) exits vapor-gas condensing device 42, but at a position or location upstream from (i.e., before) vapor-gas output assembly 52, and at a time before vapor-gas 31 (or 46) enters vapor-gas output assembly 52 (dashed arrow 54). It is critically important for vapor-gas explosiveness level measuring mechanism 50 to measure at least an indication of, and preferably determine, the explosiveness level (EL) of vapor-gas 31, followed by comparing the measurement (EL) of vapor-gas 31 to the pre-determined threshold explosiveness level (PDTEL), in order to then determine whether or not the measurement (EL) of vapor-gas 31 exceeds the pre-determined threshold explosiveness level (PDTEL), at a position or location upstream from (i.e., before) vapor-gas output assembly 52, at a time before vapor-gas 31 enters vapor-gas output assembly 52 (dashed arrow 56). Such procedure is performed in order to prevent the possibility of an 'unsafe' scenario and accompanying conditions wherein vapor-gas 31 having an explosiveness level (EL) exceeding the pre-determined threshold explosiveness level (PDTEL), passes through and exits vapor-gas output assembly 52, followed by entering second fluid processing unit 18 (FIG. 1), where processing of vapor-gas 31 by second fluid processing unit 18 could lead to an explosion caused by combustion (ignition, burning) of such explosive vapor-gas 31.

In some embodiments of the present invention, the pre-determined threshold explosiveness level (PDTEL) is equal to 75% (0.75) of the LEL (Lower Explosion Limit) of the vapor-gas. In some embodiments of the present invention, the pre-determined threshold explosiveness level (PDTEL) is equal to 50% (0.50) of the LEL (Lower Explosion Limit) of the vapor-gas. In some embodiments of the present invention, the pre-determined threshold explosiveness level (PDTEL) is equal to 25% (0.25) of the LEL (Lower Explosion Limit) of the vapor-gas.

Figure 4:
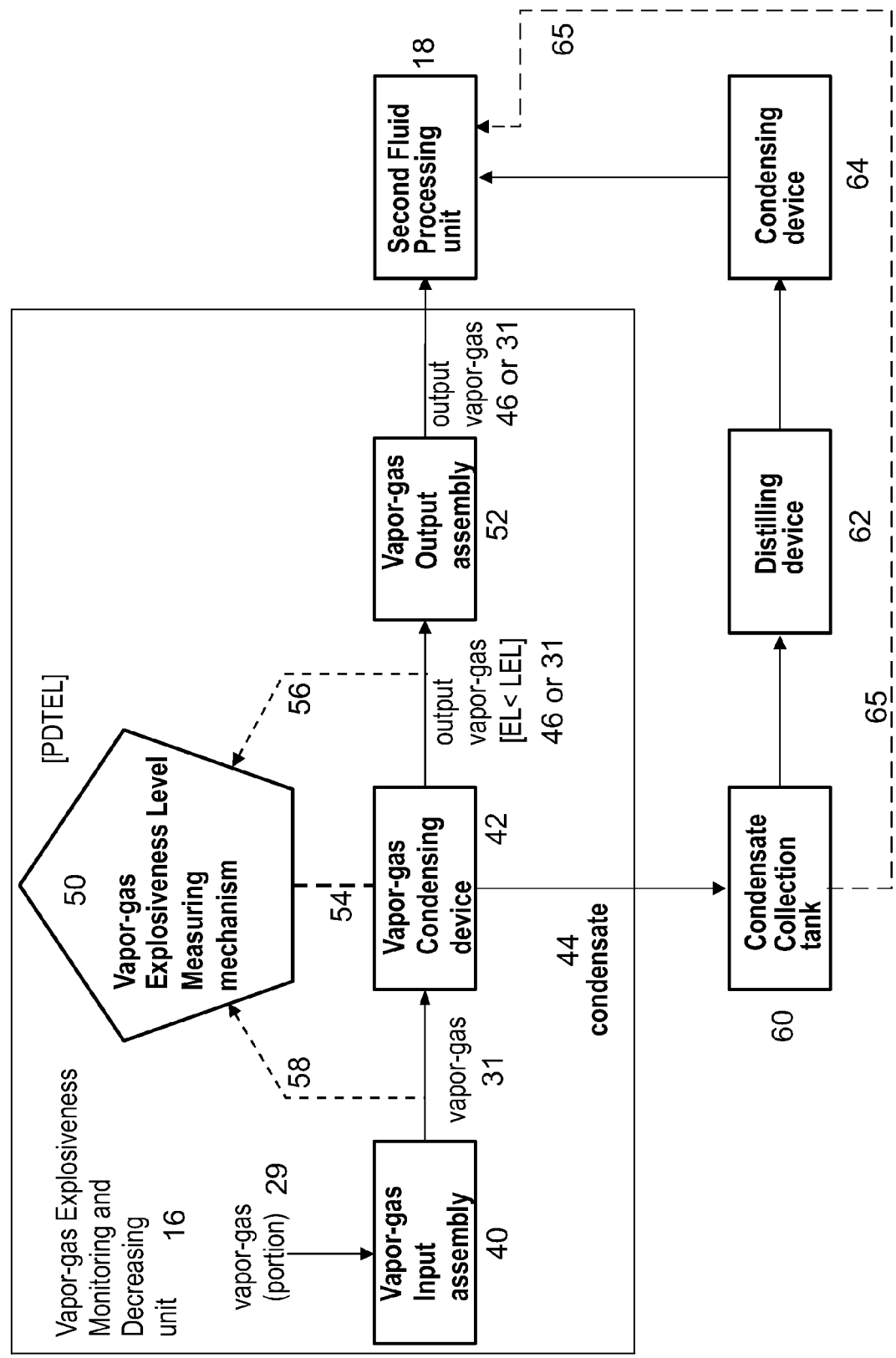
FIG. 4 is a schematic diagram illustrating an exemplary embodiment of the vapor-gas explosiveness monitoring and decreasing unit (as illustrated in FIG. 3), shown operatively connected to (optional) additional fluid processing components, in accordance with the present invention.

FIG. 4 is a schematic diagram illustrating an exemplary embodiment of the vapor-gas explosiveness monitoring and decreasing unit 16 (as illustrated in FIG. 3), shown operatively connected to (optional) additional fluid processing components (for example, a condensate collection tank 60, a distilling device 62, and a condensing device 64), in accordance with the present invention.

According to an embodiment shown in FIG. 4, either during, or following activation and operation of vapor-gas explosiveness monitoring and decreasing unit 16, and of vapor-gas condensing device 48, condensate 44 exits from condensing device 48, and enters condensate collection tank 60, for collection. Collected condensate 44 is then fed into distilling device 62, for distillation. The distillate generated by distilling device 62 is then fed into condensing device 64, for forming a condensate. This condensate is then fed into second fluid processing unit 18, and is used by second fluid processing unit 18 for processing output vapor-gas 46 (or 31).

According to another embodiment shown in FIG. 4, either during, or following activation and operation of vapor-gas explosiveness monitoring and decreasing unit 16, and of vapor-gas condensing device 48, condensate 44 exits from condensing device 48, and enters condensate collection tank 60, for collection. As indicated by dashed arrow referenced by 65, collected condensate 44 is then directly fed into second fluid processing unit 18, and is used by second fluid processing unit 18 for processing output vapor-gas 46 (or 31).

FIG. 5 is a schematic diagram illustrating an exemplary embodiment of the main components, and additional fluid processing components, of a system (safe (liquid) fluid processing system 70) for safely processing (decontaminating, purifying) a contaminated (liquid) fluid, such as contaminated water (wastewater), via monitoring and decreasing explosiveness of vapor-gas species formed therefrom, which can be used for implementing the exemplary embodiment of the method presented in FIG. 1, in accordance with the present invention.

With reference to FIG. 5, along with reference to FIGS. 1, 2, and 3, some embodiments of safe (liquid) fluid processing system 70) for safely processing (decontaminating, purifying) a contaminated (liquid) fluid, such as contaminated water (wastewater), for example, supplied by, or obtained from, fluid (liquid) source 72, include the following main components and functionalities thereof: fluid (liquid) input unit 74, configured for receiving and transporting the (liquid) fluid (block 2, FIG. 1); first fluid (liquid) processing unit 76, configured for being operatively connected to fluid (liquid) input unit 74, for receiving and processing the (liquid) fluid, and for forming a processed (liquid) fluid including a vapor-gas portion 78 (block 4, FIG. 1); vapor-gas explosiveness monitoring and decreasing unit 16, configured for being operatively connected to first fluid (liquid) processing unit 76, for receiving, and, for measuring at least an indication of explosiveness level of, vapor-gas portion 78, wherein if the measurement of vapor-gas portion 78 exceeds a pre-determined threshold explosiveness level (PDTEL), then part of vapor-gas portion 78 is condensed, for forming a condensate 80, and an output vapor-gas 82 whose explosiveness level is less than lower explosion limit (LEL) of output vapor-gas 82 (block 6, FIG. 1); and second fluid (vapor-gas) processing unit 84, configured for being operatively connected to vapor-gas explosiveness monitoring and processing unit 16, for receiving and processing output vapor-gas 82, and for forming a processed vapor-gas product, for example, hot gases 86, (block 8, FIG. 1).

In some embodiments of safe (liquid) fluid processing system 70, processed vapor-gas product (hot gases) 86 is fed into a (non-aqueous) heat exchanger and a (water) heat exchanger, for use in continued operation of safe (liquid) fluid processing system 70 for processing (decontaminating, purifying) the contaminated (liquid) fluid (contaminated water (wastewater)).

Some embodiments of safe (liquid) fluid processing system 70 further include: output unit 88, configured for being operatively connected to second fluid (vapor-gas) processing unit 84, for receiving and transporting exhaust gas 90 from second fluid (vapor-gas) processing unit 84, for example, via a vent 92.

Some embodiments of safe (liquid) fluid processing system 70 further include a central process control unit (for example, 22, FIG. 2), configured for being operatively connected to each of fluid (liquid) input unit 74, first fluid (liquid) processing unit 76, vapor-gas explosiveness monitoring and decreasing unit 16, second fluid (vapor-gas) processing unit 84, and optionally, output unit 88, for enabling central process control of each of these system units.

As shown in FIG. 5, in the exemplary embodiment of safe (liquid) fluid processing system 70, second fluid (vapor-gas) processing unit 84 includes an oxidizer 94, such as a thermal oxidizer (for example, a regenerative thermal oxidizer (RTO), [e.g., as disclosed in references 1, 2]), for thermally oxidizing, and therefore, for thermally destroying, the vapor-gas phase volatile (combustible) water contaminants contained in output vapor-gas 82.

FIG. 6 is a schematic diagram illustrating an exemplary embodiment of the main components, and additional fluid processing components, of a system (safe (vapor-gas) fluid processing system 100) for safely processing (decontaminating, purifying) a contaminated (vapor-gas) fluid, such as contaminated air (waste exhaust), via monitoring and decreasing explosiveness of vapor-gas species contained therein, which can be used for implementing the exemplary embodiment of the method presented in FIG. 1, in accordance with the present invention.

With reference to FIG. 6, along with reference to FIGS. 1, 2, and 3, some embodiments of safe (vapor-gas) fluid processing system 100) for safely processing (decontaminating, purifying) a contaminated (vapor-gas) fluid, such as contaminated air (waste exhaust), for example, supplied by, or obtained from, fluid (vapor-gas) source 102, include the following main components and functionalities thereof: fluid (vapor-gas) input unit 104, configured for receiving and transporting the (vapor-gas) fluid (block 2, FIG. 1); first fluid (vapor-gas) processing unit 106, configured for being operatively connected to fluid (vapor-gas) input unit 104, for receiving and processing the (vapor-gas) fluid, and for forming a processed (vapor-gas) fluid including a vapor-gas portion 108 (block 4, FIG. 1); vapor-gas explosiveness monitoring and decreasing unit 16, configured for being operatively connected to first fluid (vapor-gas) processing unit 106, for receiving, and, for measuring at least an indication of explosiveness level of, vapor-gas portion 108, wherein if the measurement of vapor-gas portion 108 exceeds a pre-determined threshold explosiveness level (PDTEL), then part of vapor-gas portion 108 is condensed, for forming a condensate 110, and an output vapor-gas 112 whose explosiveness level is less than lower explosion limit (LEL) of output vapor-gas 112 (block 6, FIG. 1); and second fluid (vapor-gas) processing unit 114, configured for being operatively connected to vapor-gas explosiveness monitoring and processing unit 16, for receiving and processing output vapor-gas 112, and for forming a processed vapor-gas product, for example, hot gases 116, (block 8, FIG. 1).

In some embodiments of safe (vapor-gas) fluid processing system 100, processed vapor-gas product (hot gases) 116 is fed into a (water) heat exchanger, for use in continued operation of safe (vapor-gas) fluid processing system 100 for processing (decontaminating, purifying) the contaminated (vapor-gas) fluid (contaminated air (waste exhaust)).

Some embodiments of safe (vapor-gas) fluid processing system 100 further include: output unit 118, configured for being operatively connected to second fluid (vapor-gas) processing unit 114, for receiving and transporting exhaust gas 120 from second fluid (vapor-gas) processing unit 114, for example, via a vent 122.

Some embodiments of safe (vapor-gas) fluid processing system 100 further include a central process control unit (for example, 22, FIG. 2), configured for being operatively connected to each of fluid (vapor-gas) input unit 104, first fluid (vapor-gas) processing unit 106, vapor-gas explosiveness monitoring and decreasing unit 16, second fluid (vapor-gas) processing unit 114, and optionally, output unit 118, for enabling central process control of each of these system units.

As shown in FIG. 6, in the exemplary embodiment of safe (vapor-gas) fluid processing system 100, second fluid (vapor-gas) processing unit 114 includes an oxidizer 124, such as a thermal oxidizer (for example, a regenerative thermal oxidizer (RTO), [e.g., as disclosed in references 1, 2]), for thermally oxidizing, and therefore, for thermally destroying, the vapor-gas phase volatile (combustible) air (waste exhaust) contaminants contained in output vapor-gas 110.

Example (Prophetic)

Selected embodiments of the present invention, including novel and inventive aspects, characteristics, special technical features, and advantages thereof, as illustratively described hereinabove, and as claimed in the claims section hereinbelow, are exemplified and have experimental support in the following (prophetic) example, which is not intended to be limiting.

For this (prophetic) example, reference is made to FIG. 5, a schematic diagram illustrating an exemplary embodiment of the main components, and additional fluid processing components, of a system for safely processing (decontaminating, purifying) a contaminated (liquid) fluid, such as contaminated water (wastewater), via monitoring and decreasing explosiveness of vapor-gas species formed therefrom, which can be used for implementing the exemplary embodiment of the method presented in FIG. 1, in accordance with the present invention.

A steam stripper produces 2000 $m^3$ 90° C. exhaust/hour, including 317 kilogram VOC/hour and about 400 kilogram water/hour.

Vapor-gas exiting the steam stripper is directed as a process vapor-gas to a three-chambered RTO (regenerative thermal oxidizer) having a capacity to safely dispose of not more than 9 gram VOC/m$^3$ of air as a mixture of air as an oxidation agent and the organic vapors which is 25% of the LEL (Lower Explosion Limit).

A water-cooled vapor-gas condensing device, operatively connected to a vapor-gas input assembly, to a vapor-gas explosiveness level measuring mechanism, and to a vapor-gas output assembly, as illustrated hereinabove in FIG. 3, is placed before the process gas inlet of the RTO upstream of the oxidation agent inlet. Water having a temperature of 30° C. is passed through the condenser, leading to formation of a 320 kilogram/hour condensate having a 1:1 weight ratio of water to VOC (volatile organic compounds).

The process vapor-gas from which the condensate is removed enters the RTO with a concentration of 9 gram VOC/m$^3$ after mixing with an additional 15000 m$^3$/hour of air at 120° C. (heated using the heat produced by combustion with the help of a heat exchanger) as an oxidation agent through the main RTO inlet. The mixture of process vapor-gas with oxidation agent passes through a heating heat exchanger of the RTO to absorb heat, but does not explode as the VOC concentration is well below the LEL and then enters the combustion chamber of the RTO.

Concurrently with the passage of the process vapor-gas/oxidation agent mixture through the combustion chamber, the condensate is injected directly into the combustion chamber of the RTO as an atomized spray. As sufficient oxidation agent has been introduced as air, there is sufficient oxidation agent to allow oxidation of all the VOC.

In such a way, substantially all of the VOC in the steam stripper exhaust is destroyed and not released into the atmosphere and substantially all the heat from the combustion of the VOC is recovered but the process vapor-gas in the heating heat exchanger of the RTO never exceeds safe limits, so there is little risk of an explosion.

Above, embodiments have been discussed with reference to a two-bed RTO. In embodiments, the present invention is implemented with a three-bed or greater bed RTO.

It is to be fully understood that certain aspects, characteristics, and features, of the present invention, which are illustratively described and presented in the context or format of a plurality of separate embodiments, may also be illustratively described and presented in any suitable combination or sub-combination in the context or format of a single embodiment. Conversely, various aspects, characteristics, and features, of the present invention, which are illustratively described and presented in combination or sub-combination in the context or format of a single embodiment, may also be illustratively described and presented in the context or format of a plurality of separate embodiments.

Although the invention has been illustratively described and presented by way of specific embodiments, and examples thereof, it is evident that many alternatives, modifications, and variations, thereof, will be apparent to those skilled in the art. Accordingly, it is intended that all such alternatives, modifications, and variations, fall within, and are encompassed by, the scope of the appended claims.

All patents, patent applications, and publications, cited or referred to in this specification are herein incorporated in their entirety by reference into the specification, to the same extent as if each individual patent, patent application, or publication, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

REFERENCES

1. U.S. Pat. No. 7,455,781, to Levin, of same applicant/assignee as the present invention, entitled: "Method And system Of Destruction Of Volatile Compounds In Wastewater".
2. WIPO PCT Pat. Appl. Int'l. Pub. No. WO 2008/026196, published Mar. 6, 2008, of PCT Pat. Appl. No. PCT/IL2006/001016, filed Aug. 31, 2006, of same applicant/assignee as the present invention, entitled: "Method And Device For Waste-water Purification".

What is claimed is:

1. A method for safely processing a fluid, the method comprising:
   receiving and transporting the fluid;
   processing the fluid, for forming a processed fluid including a vapor-gas portion;
   measuring at least an indication of explosiveness level of said vapor-gas portion, wherein if said measurement of said vapor-gas portion exceeds a pre-determined threshold explosiveness level (PDTEL), then part of said vapor-gas portion is condensed, for forming a condensate, and an output vapor-gas whose explosiveness level is less than lower explosion limit (LEL) of said output vapor-gas; and processing said output vapor-gas, for forming processed vapor-gas product.

2. The method of claim 1, wherein said pre-determined threshold explosiveness level (PDTEL) is equal to at least 25% (0.25) of said LEL (lower explosion limit) of said vapor-gas portion.

3. The method of claim 1, wherein if said measurement of said vapor-gas portion does not exceed said pre-determined threshold explosiveness level (PDTEL), then said vapor-gas portion is not condensed, for forming (non-condensed) output vapor-gas whose said explosiveness level is less than said lower explosion limit (LEL) of said output vapor-gas.

4. The method of claim 1, wherein said part of said vapor-gas portion is condensed by a vapor-gas condensing device.

5. The method of claim 4, wherein said vapor-gas condensing device is activated by a vapor-gas explosiveness level measuring mechanism.

6. The method of claim 1, wherein said measuring is performed by a vapor-gas explosiveness level measuring mechanism.

7. The method of claim 1, wherein said part of said vapor-gas portion is condensed by a vapor-gas explosiveness monitoring and decreasing unit.

8. The method of claim 7, wherein said vapor-gas explosiveness monitoring and decreasing unit includes a vapor-gas condensing device for said condensing of said part of said vapor-gas portion.

9. The method of claim 8, wherein said vapor-gas explosiveness monitoring and decreasing unit further includes a vapor-gas explosiveness level measuring mechanism for said measuring of said indication of said explosiveness level of said vapor-gas portion.

10. The method of claim 1, wherein said measuring is performed at a position or location downstream from a vapor-gas condensing device, at a time after said output vapor-gas exits a vapor-gas condensing device.

11. The method of claim 10, wherein the step of measuring is also performed at a position or location upstream from a vapor-gas output assembly, at a time before said output vapor-gas enters a vapor-gas output assembly.

12. The method of claim 1, wherein said measuring is first performed at a position or location downstream from a vapor-gas input assembly, at a time after said vapor-gas portion exits a vapor-gas input assembly.

13. The method of claim 11, wherein said measuring is also performed at a position or location upstream from a vapor-gas condensing device, at a time before said vapor-gas portion enters said vapor-gas condensing device.

14. The method of claim 13, wherein said measuring is also performed at a position or location downstream from said vapor-gas condensing device, at a time after said output vapor-gas exits said vapor-gas condensing device.

15. The method of claim 1, wherein said processing of said output vapor-gas is performed by an oxidizer.

16. The method of claim 15, wherein said oxidizer is a thermal oxidizer, or, a regenerative thermal oxidizer.

17. A method for monitoring and decreasing explosiveness of a vapor-gas, the method comprising:
receiving and transporting the vapor-gas;
measuring at least an indication of explosiveness level of the vapor-gas, wherein if said measurement of the vapor-gas exceeds a pre-determined threshold explosiveness level (PDTEL), then part of the vapor-gas is condensed, for forming a condensate, and an output vapor-gas whose explosiveness level is less than lower explosion limit (LEL) of said output vapor-gas; and
receiving and transporting said output vapor-gas.

18. The method of claim 17, wherein said pre-determined threshold explosiveness level (PDTEL) is equal to at least 25% (0.25) of said LEL (lower explosion limit) of the vapor-gas.

19. The method of claim 17, wherein if said measurement of said vapor-gas portion does not exceed said pre-determined threshold explosiveness level (PDTEL), then the vapor-gas is not condensed, for forming (non-condensed) output vapor-gas whose said explosiveness level is less than said lower explosion limit (LEL) of said output vapor-gas.

20. The method of claim 17, wherein said part of the vapor-gas is condensed by a vapor-gas condensing device.

21. The method of claim 20, wherein said vapor-gas condensing device is activated by a vapor-gas explosiveness level measuring mechanism.

22. The method of claim 17, wherein said measuring is performed by a vapor-gas explosiveness level measuring mechanism.

23. The method of claim 17, wherein said part of the vapor-gas is condensed by a vapor-gas explosiveness monitoring and decreasing unit.

24. The method of claim 23, wherein said vapor-gas explosiveness monitoring and decreasing unit includes a vapor-gas condensing device for said condensing of said part of the vapor-gas.

25. The method of claim 24, wherein said vapor-gas explosiveness monitoring and decreasing unit further includes a vapor-gas explosiveness level measuring mechanism for said measuring of said indication of said explosiveness level of the vapor-gas.

26. The method of claim 17, wherein said measuring is performed at a position or location downstream from a vapor-gas condensing device, at a time after said output vapor-gas exits a vapor-gas condensing device.

27. The method of claim 26, wherein said measuring is also performed at a position or location upstream from a vapor-gas output assembly, at a time before said output vapor-gas enters a vapor-gas output assembly.

28. The method of claim 17, wherein said measuring is first performed at a position or location downstream from a vapor-gas input assembly, at a time after the vapor-gas exits a vapor-gas input assembly.

29. The method of claim 28, wherein said measuring is also performed at a position or location upstream from a vapor-gas condensing device, at a time before the vapor-gas enters said vapor-gas condensing device.

30. The method of claim 29, wherein said measuring is also performed at a position or location downstream from said vapor-gas condensing device, at a time after said output vapor-gas exits said vapor-gas condensing device.

31. The method of claim 17, wherein said output vapor-gas is processed by an oxidizer.

32. The method of claim 31, wherein said oxidizer is a thermal oxidizer, or, a regenerative thermal oxidizer.

* * * * *